US011793602B2

(12) United States Patent
Sorenson et al.

(10) Patent No.: US 11,793,602 B2
(45) Date of Patent: Oct. 24, 2023

(54) DENTAL COMPOSITIONS AND RELATED METHODS OF USE

(71) Applicant: Ultradent Products, Inc., South Jordan, UT (US)

(72) Inventors: Robert Edward Sorenson, South Jordan, UT (US); Andy Takashi Kawamoto, Sandy, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 928 days.

(21) Appl. No.: 16/414,592

(22) Filed: May 16, 2019

(65) Prior Publication Data

US 2019/0350677 A1 Nov. 21, 2019

Related U.S. Application Data

(60) Provisional application No. 62/672,350, filed on May 16, 2018.

(51) Int. Cl.
*A61C 5/30* (2017.01)
*A61K 6/17* (2020.01)
*A61K 6/70* (2020.01)

(52) U.S. Cl.
CPC ............ *A61C 5/30* (2017.02); *A61K 6/17* (2020.01); *A61K 6/70* (2020.01)

(58) Field of Classification Search
CPC .............. A61C 5/30; A61K 6/70; A61K 6/17
USPC ....................................................... 433/228.1
See application file for complete search history.

(56) References Cited

U.S. PATENT DOCUMENTS

| 1,935,418 | A | * | 11/1933 | Salzmann | A61K 6/71 106/35 |
| 4,874,315 | A | * | 10/1989 | Featherstone | A61C 5/00 106/35 |
| 5,427,613 | A | * | 6/1995 | Arnold | A61K 6/847 106/35 |
| 5,735,942 | A | * | 4/1998 | Litkowski | A61K 8/25 106/35 |
| 5,749,733 | A | * | 5/1998 | Qian | A61K 6/60 106/35 |
| 6,093,084 | A | * | 7/2000 | Jefferies | A61K 6/30 451/37 |

(Continued)

FOREIGN PATENT DOCUMENTS

| CN | 101518499 | 3/2011 |
| DE | 102008028306 | 12/2009 |
| WO | 2010060653 | 6/2010 |

OTHER PUBLICATIONS

International Search Report and Written Opinion dated Sep. 19, 2019 for PCT/US2019/032711.

(Continued)

*Primary Examiner* — Matthew M Nelson
(74) *Attorney, Agent, or Firm* — Maschoff Brennan

(57) ABSTRACT

Dental compositions (e.g., adhesives, cements, primers, sealants, and etchants) and related methods of use are disclosed herein. The dental compositions can include diamond particles. The diamond particles can have an average size of below 10 microns. In some instances, the dental adhesives can act as a one-part dental adhesive, and can be configured to remove portions of the smear layer and act as an adhesive or bonding agent.

20 Claims, 4 Drawing Sheets

(56) References Cited

U.S. PATENT DOCUMENTS

| | | | |
|---|---|---|---|
| 6,494,716 B1* | 12/2002 | Dorn | A61K 6/65 |
| | | | 424/49 |
| RE48,318 E * | 11/2020 | Kwon | A61C 13/225 |
| 2009/0035728 A1* | 2/2009 | Aasen | A61K 49/221 |
| | | | 433/226 |
| 2009/0130031 A1* | 5/2009 | Herman | B82Y 5/00 |
| | | | 424/49 |
| 2010/0136069 A1* | 6/2010 | Deckner | A61K 8/922 |
| | | | 424/57 |
| 2023/0165759 A1* | 6/2023 | Morisaki | A61K 6/64 |
| | | | 433/228.1 |

OTHER PUBLICATIONS

Gronwald, et al., The Influence of Suspension containing Nanodiamonds on the Morphology of the Tooth Tissue Surface in Atomic Force Microscope Observations, BioMed Research International, vol. 2018,Artice ID 9856851 ,2018 ,9 pgs.

Lee, et al., Clinical Validation of a Nonodiamond-Embeded Thermoplastic Biomaterial, PNAS, Edited by University of Southern California Biomedical Engineering Department , Jul. 4, 2017.

Perchyonok, et al., Bio-Functional Nanodiamond Restorative Meterials Containing Bio-Additives: In Vitro Approach, Open Journal of Stomatology, vol. 5 , May 2015 ,117-126.

* cited by examiner

DENTAL COMPOSITIONS AND RELATED METHODS OF USE

RELATED APPLICATIONS

This application claims priority to U.S. Provisional Application No. 62/672,350, filed on May 16, 2018, and titled "DENTAL ADHESIVES AND RELATED METHODS OF USE," which is incorporated herein by reference in its entirety.

TECHNICAL FIELD

The present disclosure relates generally to dental compositions, including dental adhesives, sealants, cements, primers, and etchants. More specifically, the present disclosure relates to dental compositions (such as dental adhesives, dental sealants, dental cements, dental primers, and dental etchants) containing diamond particles.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1:
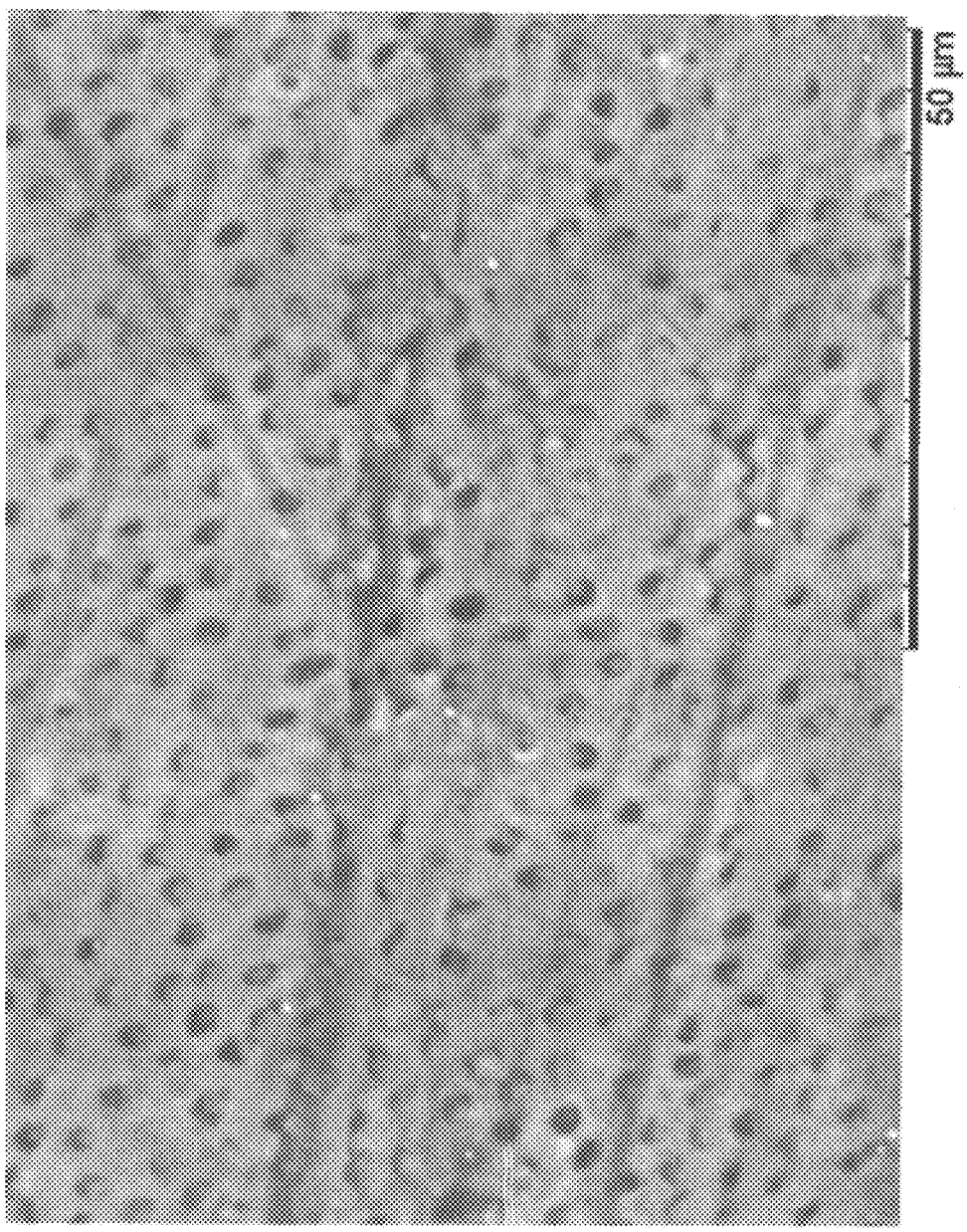
FIG. 1 is an image of a tooth surface after treatment with an adhesive composition in accordance with an embodiment of the present disclosure.

The present disclosure relates to dental compositions and related methods of use. The dental compositions include, but are not limited to, dental adhesives, dental sealants, dental cements, dental primers, and dental etchants. As further discussed below, diamond particles can be incorporated into the dental compositions to provide the compositions with one or more desired characteristics. For example, diamond particles can be dispersed throughout a carrier of the dental compositions to achieve desired properties. The dental compositions can also be used in various dental procedures, including dental restoration and/or restorative procedures. Other uses are also contemplated.

In one embodiment, the present disclosure relates to dental adhesives that can be used, for example, in dental restoration and/or restorative procedures. Traditional restoration procedures include use of a dental bur (or other instrument) to remove material from a tooth structure. Removal of such material can result in a smear layer on a surface of the tooth being treated. This smear layer can include portions of tooth materials (e.g., dentin, enamel), fluid, and/or enzymes, and can further extend into the dentin tubules.

The dental adhesives disclosed herein can be used to remove portions of the smear layer from the surface of the tooth and the dentin tubules, as well as debris from the smear layer deposited into the dentin tubules that form dentin plugs. The dental adhesives can also abrade the surface of the tooth material (e.g., enamel and dentin) or dental restoration materials (e.g., metals (e.g., stainless steel and gold), ceramics (e.g., zirconia and lithium disilicate), hybrid ceramics, cements, composites, and porcelain) to create a rough, porous, or microporous surface that facilitates bonding. The dental adhesives can also adhere and/or bond one or more restorative materials to the tooth structure and/or a dental restoration material. In such embodiments, the dental adhesives can be referred to as one-part dental adhesives or universal dental adhesives, as the adhesives can be configured to remove portions of the smear layer and/or abrade surfaces of the tooth material and/or restoration material while acting as an adhesive or bonding agent. In some embodiments, the dental adhesives disclosed herein can reduce, minimize, and/or eliminate the need for an abrasion act (e.g., air abrasion or etching) and can replace conventional etch-and-rinse or self-etching adhesives. In addition, the dental adhesives can provide a primerless system for adhering dental restoration compounds to teeth. In some embodiments, the dental adhesives can also penetrate or otherwise extend into one or more of the dentin tubules, increasing the bonding strength between the restorative material and the tooth structure.

These dental adhesives can also be described as dental adhesive compositions or abrasive compositions, and can comprise various components. For example, in some embodiments, the dental adhesives comprise one or more abrasive materials or abrasive agents. The dental adhesives can further comprise one or more carriers for the abrasive agents. In some embodiments, the dental adhesives comprise polymerizable materials (e.g., one or more monomers or polymerizable monomers). Additional components can also be included, such as solvents, rheology and/or viscosity modifiers, polymerization accelerators, polymerization initiators, preservatives, antimicrobials, colorants, pigments, and/or fillers, etc.

Various types of abrasive materials can be included in the dental adhesives disclosed herein. The abrasive materials can be relatively inert, or substantially chemically inactive. The abrasive materials can also be relatively hard. For example, the abrasive materials can comprise a hardness that is greater than the hardness of a tooth structure, dental smear material, and/or dental restoration material. When scrubbed or otherwise rubbed against dental smear and/or a smear layer on a tooth surface, the abrasive materials can be configured to abrade or otherwise remove a portion of the dental smear from the tooth surface and/or dentin tubules. The abrasive materials can also be configured to abrade or otherwise remove a portion of the tooth structure or dental restoration material to provide a rough, porous, or microporous surface.

As an example, the abrasive materials can comprise particles comprising any one of diamond, fullerene structures (including carbon nanotubes, nanowires, and nanorods), graphene, lonsdaleite, cubic boron nitride, or combinations thereof. In particular embodiments, the abrasive materials comprise diamond particles.

The particles of the abrasive material can be various sizes. For instance, in some embodiments, the particles have an average size (e.g., average diameter) of about 10 µm or less, such as between about 0.5 nm and about 10 µm. In other embodiments, microparticles are used. Microparticles can refer to particles having an average size (e.g., average diameter) of between about 100 nm and about 10 µm. In yet other embodiments, nanoparticles are used. Nanoparticles can refer to particles having an average size (e.g., average diameter) of about 100 nm or less, such as between about 0.5 nm and about 100 nm.

As set forth above, in some embodiments, the abrasive materials comprise diamond particles, diamond microparticles, and/or diamond nanoparticles. Such diamond particles, microparticles, and/or nanoparticles can be generated in various ways, including, but not limited to, by impact, such as by explosive detonation or meteoric impacts, by chemical vapor deposition (CVD), or by removal from amorphous carbon. Diamond nanoparticles can also be referred to as nanodiamonds.

In some embodiments, the dental adhesives comprise diamond nanoparticles having an average size of between about 0.5 nm and about 100 nm, between about 1 nm and about 50 nm, or between about 5 nm and about 10 nm. In further embodiments, the dental adhesives comprise diamond nanoparticles having an average size of less than about 100 nm, less than about 50 nm, less than about 20 nm, or less than about 10 nm. Other sizes of nanoparticles can also be used.

While not wishing to be bound by any particular theory, the use of particles having reduced size, such as nanodiamond particles, may prevent the particles from agglomerating and/or falling out of the solution or mixture with the other components of the dental adhesives.

The amount of abrasive materials (e.g., diamond particles) included in the dental adhesives can vary. For example, in certain embodiments, the dental adhesives comprise between about 0.1% and about 20% by weight of abrasive materials (e.g., diamond particles). In other embodiments, the dental adhesives comprise between about 0.1% and about 15%, between about 0.1% and about 10%, between about 0.1% and about 5%, between about 0.5% and about 2.5%, or between about 1% and about 2.5% by weight of abrasive materials (e.g., diamond particles). Other amounts can also be used.

The dental adhesives can also comprise a carrier in which the abrasive materials can be dispersed. In some embodiments, the carrier comprises a polymerizable material. Various types of polymerizable materials, such as monomers, dimers, and oligomers can be used. The monomers can also be described as polymerizable monomers, as one or more monomers can polymerize with one or more other monomers (which can be the same or different) to form a polymer or copolymer. In some embodiments, the dental adhesives comprise one or more acrylic monomers, vinyl-containing monomers, silicon-containing monomers, and/or thiol containing monomers. And in certain embodiments, the dental adhesives comprise one or more acrylate monomers, acrylamide monomers, or mixtures thereof. In further embodiments the dental adhesives comprise one or more acrylic monomers selected from the group consisting of methacrylate monomers (or methacrylic monomers), methacrylamide monomers, and mixtures thereof. And in still further embodiments, the dental adhesives comprise at least one methacrylate monomer (or at least one methacrylic monomer) and at least one methacrylamide monomer.

Exemplary polymerizable materials that can be used in the dental adhesives include, but are not limited to, hydroxy alkyl methacrylates (e.g., hydroxyethyl methacrylate, 2-hydroxyethyl methacrylate (2-HEMA), hydroxyethyl methacrylate succinate, etc.), ethylene glycol methacrylates (e.g., polyethylene glycol methacrylates, triethylene glycol dimethactylates, etc.), diol dimethacrylates, bisphenol methacrylates (e.g., bisphenol glycidyl methacrylate (bis-GMA), ethoxylated bisphenol A dimethacrylate (EBP-DMA), etc.), urethane methacrylates (e.g., polyurethane dimethacrylates (PUDMA), diurethane dimethacrylates (DUDMA), etc.), polycarbonate methacrylates (e.g., polycarbonate dimethacrylate (PCDMA)), silicon-containing monomers (e.g., silsesquioxanes such as polyhedral oligomeric silsesquioxanes, methacrylic polyhedral oligomeric silsesquioxane (methacrylic POSS), siloxanes, etc.), phosphate-containing monomers (e.g., 10-methacryloyloxydecyl dihydrogen phosphate (MDP)), glucarodilactone methacrylate (GDMA-P), vinyl monomers (e.g., methyl methacrylate (MMA), butyl methacrylate (BMA), N-vinylpyrrolidinone, methacrylic acid, etc.), acrylamides (e.g., N, N dimethylacrylamide (DMAA)), polythiols (e.g., pentaerythritol tetramercaptopropionate), alkyl thiols (e.g., 1-Octanethiol, 1,6-Hexanedithiol, etc.), thiopropionic acid and esters thereof (e.g., butyl 3-mercaptopropionate), and mixtures and/or derivatives thereof. Other materials can also be used.

The amount of polymerizable materials (e.g., monomers) included in the dental adhesives can vary. In one embodiment, the dental adhesives comprise between about 40% and about 90% by weight of one or more polymerizable materials (e.g., monomers). In other embodiments, the dental adhesives comprise between about 45% and about 90% by weight, between about 50% and about 85% by weight, between about 55% and about 85% by weight, between about 60% and about 80% by weight, between about 65% and about 80% by weight, or between about 70% and about 80% by weight of one or more polymerizable materials (e.g., monomers). Other amounts can also be used.

In certain embodiments, the carrier further comprises one or more solvents. For example, the dental adhesives can comprise one or more polar solvents. While not wishing to be bound by any particular theory, the use of polar solvents can prevent the nanodiamond particles from agglomerating and/or falling out of the solution or mixture with the other components of the dental adhesive. Exemplary solvents that can be used include, but are not limited to, water, alcohol(s) (e.g., ethanol), and/or acetone. In one embodiment, the dental adhesives comprise water and ethanol. In some embodiments, the dental adhesives comprise between about 5% and about 25% by weight, between about 5% and about 20% by weight, or between about 10% and about 20% by weight of one or more solvents. In particular embodiments, the dental adhesive composition is stored in a solution.

One or more additional components can also be included in the dental adhesives to achieve desired properties. For example, in certain embodiments, the dental adhesives comprise one or more initiators and/or accelerators, which can also be referred to as polymerization initiators and/or polymerization accelerators. As can be appreciated, initiators and/or accelerators can interact or otherwise react with one or more polymerizable materials (e.g., monomers) to initiate and/or accelerate polymerization of the one or more polymerizable materials (e.g., monomers). In some embodiments, initiators and/or accelerators are used to increase the curability of the dental adhesives. For example, initiators and/or accelerators can be used to increase the curing rate of the dental adhesives.

In some embodiments, one or more photoinitiators are used. And in particular embodiments, blends of initiators and/or accelerators are used, such as blends of photoinitiators. Exemplary initiators and/or accelerators that can be used include, but are not limited to, α-diketone initiators and/or accelerators (e.g., camphorquinone, benzyl, 2,3-pentanedione, etc.), phosphine oxide initiators and/or accelerators (e.g., trimethylbenzoyl-diphenyl-phosphine oxide), dialkylaminobenzoic acid ester initiators and/or accelerators (e.g., ethyl 4-(dimethylamino)benzoate), xanthanones, imidazoles, idonium salts, phosphonates, and mixtures thereof. Other types of initiators and/or accelerators can also be used, including peroxides (e.g., benzoyl peroxide) and the like.

In a particular embodiment, the dental adhesives comprise a blend or mixture of two or more of an α-diketone initiator and/or accelerator (e.g., camphorquinone), a phosphine oxide initiator and/or accelerator (e.g., trimethylbenzoyl-diphenyl-phosphine oxide), and a dialkylaminobenzoic acid ester initiator and/or accelerator (e.g., ethyl 4-(dimethylamino)benzoate). In certain embodiments, the dental adhesives comprise between about 0.1% and about 10% by weight, between about 0.1% and about 5% by weight, between about 0.5% and about 3% by weight, or between about 0.5% and about 2.5% by weight of one or more initiators and/or accelerators.

In further embodiments, initiators and/or accelerators that can be used include reducing agents. In some embodiments, the dental adhesives comprise one or more tertiary amines (aromatic and/or aliphatic tertiary amines), sulfinic acids (or salts thereof), aldehydes, or thiols. In one embodiment, the dental adhesives comprise an aromatic tertiary amine such as N,N-cyanoethylmethylaniline. Other types of initiators and/or accelerators can also be used.

The dental adhesives can further include one or more additives. Exemplary additives can include, but are not limited to, surfactants, rheology and/or viscosity modifiers, thickeners, preservatives (or polymerization inhibitors), antimicrobial agents, fillers, colorants, radiopaque agents, fluorescent agents, and/or ultraviolet absorbing agents.

Preservatives or polymerization inhibitors can be used to control, minimize, and/or prevent unwanted polymerization of the one or more polymerizable materials (e.g., monomers). By controlling unwanted polymerization, the shelf-life and/or stability of the dental adhesive composition can be increased. Exemplary preservatives (or polymerization inhibitors) that can be used include antioxidants that are capable of controlling, minimizing, and/or preventing polymerization of the one or more polymerizable materials (e.g., monomers). In one embodiment, the dental adhesives comprise nitroxyl radical compounds (e.g., 2,2,6,6-tetramethyl-1-piperidinyloxy or TEMPO) and/or radical scavengers (e.g., butylated hydroxytoluene, hydroquinones (methyl hydroquinone), and/or ascorbic acid), that can serve as a preservative or polymerization inhibitor. Other types of preservatives can also be used.

Antimicrobial agents can be used to kill and/or stop the growth of microbes or microorganisms such as bacteria. The use of antimicrobial agents can also reduce the possibility of infection during the dental procedure. Exemplary antimicrobial agents that can be used include EDTA, silver particles, quaternary ammonium molecules (e.g., quaternary ammonium methacrylate), chlorhexidine, and salts thereof, including zinc silicate particles, silver particles, glutaraldehydes, fluorides, chlorhexidine diacetate, and chlorhexidine gluconate.

Fillers can also be used. In some embodiments, fillers are used to modify one or more properties of the dental adhesives. For example, fillers can be used to increase the bond strength, coating properties, radiopacity, and/or mechanical strength of the dental adhesives. Exemplary filler materials that can be used include inorganic filler materials, organic filler materials, polymerizable filler materials, and composite filler materials that include inorganic and organic filler materials.

In some embodiments, inorganic filler materials are used. Exemplary inorganic filler materials that can be used include, but are not limited to, prepolymerized fillers, polymerizable fillers, silica, glass, ceramics, and oxides such as $Al_2O_3$, $B_2O_3$, $TiO_2$, $ZrO_2$, $BaO$, $La_2O_3$, $SrO$, $ZnO$, $CaO$, $P_2O_5$, $Li_2O$, and $Na_2O$. Such inorganic fillers may be surface-treated, such as with silane groups. Exemplary polymerizable fillers that can be used include, but are not limited to, surface-treated methacrylates such as silanated methacrylates. Other types of filler materials can also be used.

The dental adhesives can also comprise one or more acids, which can help dissolve or otherwise break down the dental smear material or other debris. In some embodiments, one or more polymerizable materials (e.g., monomers) can include acid moieties or acidic groups. For example, in some embodiments, the dental adhesives comprise one or more organic or inorganic acids, such as acrylic acid, methacrylic acid, carboxylic acid, phosphoric acid, a phosphorylated monomer, and citric acid. Other types of acids can also be used.

The dental adhesives can also comprise one or more dyes, colorants, or pigments (e.g., titanium dioxide) to modify the optical properties of the dental adhesive. For example, in some embodiments, the diamond particles (or particles) may exhibit a grayish color and titanium dioxide (or other dyes/colorants/pigments) can be added to the dental adhesive to reduce the grayish color. In other embodiments, the diamond particles (or particles) can exhibit a white color and additional colorants may not be needed.

Methods of using the dental adhesives are also disclosed herein. In particular, it is contemplated that any of the components, principles, and/or embodiments discussed above may be utilized in either a dental adhesive composition or a method of using the same. In one embodiment, the method of using a dental adhesive comprises a step of preparing a tooth surface.

In certain embodiments, preparing a tooth surface comprises grinding and/or drilling a tooth structure with a dental instrument, such as a dental bur. This grinding and/or drilling can result in the formation of smear material, or a smear layer on a surface of the tooth. The smear layer can include portions of tooth materials (e.g., enamel and dentin), fluid, and/or enzymes, and can further extend into the dentin tubules.

In some embodiments, the method comprises a washing or rinsing step. For example, the tooth structure can be washed and/or rinsed with water or another aqueous solution to remove at least a portion of the ground or drilled tooth, or a portion of the smear material.

In certain embodiments, the tooth structure can also be dried, or substantially dried, in a drying step. In some embodiments, the tooth structure can be dried by passing gas (e.g., air) over the tooth structure, such as with a gas dryer (e.g., air dryer). For example, a compressed gas dryer (e.g., a compressed air dryer) can be used to blow or otherwise pass gas (e.g., air) over the surface of the tooth structure. In certain embodiments, the tooth structure is substantially dried until there is no observable water or liquid on the surface of the tooth structure.

The method can also comprise a step of applying a dental adhesive (or a first amount of a dental adhesive) to an exposed surface of a tooth structure. During this step, a dental adhesive, such as the dental adhesives described herein, can be applied to or otherwise disposed on the surface of the tooth structure. In certain embodiments, the dental adhesive is spread over a portion of the tooth surface.

After an amount of dental adhesive is applied to the tooth structure, an abrasion or scrubbing step can be performed. For example, after being applied to or otherwise disposed on the surface of the tooth structure, the dental adhesive can be rubbed and/or scrubbed across the surface of the tooth structure. For example, the dental adhesive can be rubbed and/or scrubbed on a surface of the tooth structure for between 1 second and 30 seconds, such as for at least 3 seconds, 5 seconds, 8 seconds, 10 seconds, 15 seconds, or 20 seconds or more. The scrubbing step can be performed using a brush, such as that on a dental brush tip.

Rubbing and/or scrubbing the dental adhesive across the surface of the tooth structure can cause at least a portion of the dental smear or other debris to be removed from the tooth structure. For example, an abrasive agent (e.g., diamond particles) in the dental adhesive can cause at least a portion of the dental smear or other debris to wear away or otherwise be removed from the tooth structure. In particular embodiments, the rubbing and/or scrubbing action of the dental adhesive causes a portion of the dental smear or debris to be removed from the surface of the tooth structure. And in further embodiments, the rubbing and/or scrubbing action of the dental adhesive causes a portion of the dental smear or debris to be removed from the dentin tubules. In addition, particles of the abrasive agent may be deposited or forced into dentin tubules. The rubbing and/or scrubbing action can also cause a portion of the tooth structure to abrade away (e.g., to create a rough or porous surface).

In one embodiment, after the dental adhesive has been used to abrade away or otherwise remove a portion of the dental smear and other debris, a portion of the dental adhesive can be removed or otherwise spread across a surface of the tooth structure. For example, a portion of the dental adhesive can be removed by a tool or other dental instrument. A portion of the dental adhesive can also be removed or spread by blowing or otherwise passing gas (e.g., air) over of tooth surface. Gas (e.g., air) can also be blown or otherwise passed over the tooth surface to thin or spread the dental adhesive over the surface of the tooth structure. For example, gas (e.g., air) can be passed over the tooth surface to form a thin layer of dental adhesive over the surface of the tooth structure.

In certain embodiments, the method further comprises an adhering step. For example, with a portion of the smear material or smear layer removed, the dental adhesive can be disposed on a surface of the tooth structure. The dental adhesive can also penetrate and/or otherwise extend into one or more of the dentin tubules. With the dental adhesive in place, a crown or other dental restorative material can be placed in contact with the dental adhesive as it is applied to the tooth structure. The dental adhesive can then be cured to adhere or otherwise bond the restorative material to the tooth structure. In some embodiments, the dental adhesive can be cured with a dental curing light. For example, in certain embodiments, a curing light is applied to the dental adhesive for between about 1 second and about 30 seconds, such as for at least about 3 seconds, 5 seconds, 8 seconds, 10 seconds, or 15 seconds to at least partially cure the dental adhesive. In certain embodiments, the dental adhesive is at least partially cured before adhering the dental restorative material.

In particular embodiments, a second step of applying a dental adhesive (or a second amount of dental adhesive) is performed prior to the adhering step. For example, a second amount of dental adhesive can be applied to or otherwise disposed on the surface of the tooth structure prior to application of the crown or dental restoration material. For example, a second amount of the dental adhesive can be spread over a portion of the tooth surface. After being applied to or otherwise disposed on the surface of the tooth structure, a second abrasion or scrubbing step can be performed wherein the second amount of the dental adhesive can be rubbed and/or scrubbed across the surface of the tooth structure. For example, the second amount of the dental adhesive can be rubbed and/or scrubbed on a surface of the tooth structure for at least 3 seconds, 5 seconds, 8 seconds, 10 seconds, 15 seconds, or 20 seconds or more.

Rubbing and/or scrubbing the second amount of the dental adhesive across the surface of the tooth structure can cause at least an additional portion of the dental smear or other debris to be removed from the tooth structure. Further, in some embodiments, rubbing and/or scrubbing the second amount of the dental adhesive across the surface of the tooth structure can further remove dental smear or debris from the dentin tubules. Additionally, in some embodiments, a second amount of dental adhesive can increase the amount of dental adhesive, including the abrasive particles, that penetrates or otherwise extends into the dentin tubules, which can increase the bond strength of the dental adhesive. The rubbing and/or scrubbing action can also cause a portion of the tooth structure to abrade away (e.g., to create a rough or porous surface).

After the second amount of the dental adhesive has been used to abrade away or otherwise remove a portion of the dental smear and other debris, a portion of the second amount of the dental adhesive can be removed or otherwise spread across a surface of the tooth structure. For example, a portion of the second amount of the dental adhesive can be removed by a tool or other dental instrument. A portion of the second amount of the dental adhesive can also be removed or spread by blowing or otherwise passing gas (e.g., air) over the tooth surface. Gas (e.g., air) can also be blown or otherwise passed over the tooth surface to thin or spread the second amount of the dental adhesive over the surface of the tooth structure. For example, gas (e.g., air) can be passed over the tooth surface to form a thin layer of dental adhesive over the surface of the tooth structure.

In some embodiments, the adhering step can then be performed. For example, with a portion of the smear material or smear layer removed, the dental adhesive can be disposed on a surface of the tooth structure. The dental adhesive can also penetrate and/or otherwise extend into one or more of the dentin tubules. With the dental adhesive in place, a crown or other dental restorative material can be placed in contact with the dental adhesive as it is applied to the tooth structure. As previously discussed, the dental adhesive can then be cured to adhere or otherwise bond the restorative material to the tooth structure. In some embodiments, the dental adhesive can be cured with a dental curing light. For example, in certain embodiments, a curing light is applied to the dental adhesive for between about 1 and about 30 seconds, such as for at least about 3 seconds, 5 seconds, 8 seconds, 10 seconds, or 15 seconds to at least partially cure the dental adhesive. In other embodiments, a third, fourth, fifth, etc. step of applying the dental adhesive can then be employed, if desired, prior to application of the crown or other dental restoration material. Additionally, in certain embodiments, the dental adhesive is at least partially cured before adhering the dental restorative material.

It will also be appreciated that the dental adhesive can be applied to a surface of a tooth structure and/or a dental restoration material. For example, the dental adhesive can be applied to a surface of a dental restoration material in a manner that is analogous to applying the dental adhesive to the surface of a tooth. The dental adhesive can also be applied to a surface of the dental structure (tooth structure and/or dental restoration material) and used to abrade away or otherwise prepare the surface for bonding (e.g., by rubbing, scrubbing, etc.). It will thus be appreciated that various methods are contemplated, and that the methods of using the adhesive composition are not limited to the above-identified steps.

As set forth above, in another embodiment, the present disclosure relates to dental cements, primers, and sealants. The dental cements, primers, and sealants disclosed herein can be used as traditional cement materials used in the dental industry. For instance, the dental cements can be used in dental restoration and/or restorative procedures. In particular, the dental cements can be used to bond one or more restorative materials to the tooth structure and/or a dental restoration material. Illustrative structures and/or components that can be bonded with the dental cements include bridges, crowns, veneers, metallic components (e.g., retainers, braces), and the like.

Various types of dental cements are contemplated, including, but not limited to, resin cements and glass ionomer cements (e.g., resin modified glass ionomer cements). Other types of cements can also be used. The cements can also be self-curing, light curing, or both.

In particular embodiments, the dental cements disclosed herein can be a two-part composition that includes a base component and a catalyst component. For instance, the cements can be contained in a dual barrel syringe, with each component occupying a separate barrel. In other embodiments, the dental cements are a one-part composition.

Various types of dental primers and dental sealants are also contemplated, including primers that can be used to condition or prepare the surface of a dental appliance or structure made of a dental restoration material (e.g., metals (e.g., stainless steel and gold), ceramics (e.g., zirconia and lithium disilicate), hybrid ceramics, cements, composites, and porcelain, and primers that can be used to condition or prepare the surface of a tooth. Sealants that can be used include sealants that can be used to fill pits and fissures in a tooth.

The dental cements, dental primers, and dental sealants can comprise one or more abrasive materials or abrasive agents. The dental cements, dental primers, and dental sealants can further comprise a carrier. The dental cements, dental primers, and dental sealants can further comprise one or more polymerizable materials. Additional components can also be included in the dental cements, primers, and sealants, such as solvents, surfactants, rheology and/or viscosity modifiers, thickeners, polymerization accelerators, polymerization initiators, preservatives, antimicrobial agents, fillers, colorants, pigments, radiopaque agents, fluorescent agents, and/or ultraviolet absorbing agents, etc.

Without limitation, it will be appreciated that the particular components identified above for use with dental adhesives can also be incorporated into the dental cements, primers, and sealants. For example, various types of abrasive materials can be included in the dental cements, primers, and sealants. In particular, it is contemplated that any of the abrasive materials discussed above with respect to the dental adhesives can also be used in a dental cement (or the base and/or catalyst component thereof), dental primer, or dental sealant. For example, the abrasive materials can comprise diamond particles, microparticles, and/or nanoparticles.

In some embodiments, the dental cements, primers, and sealants comprise diamond nanoparticles having an average size of between about 0.5 nm and about 100 nm, between about 1 nm and about 50 nm, or between about 5 nm and about 10 nm. In further embodiments, the dental cements comprise diamond nanoparticles having an average size of less than about 50 nm, less than about 20 nm, or less than about 10 nm. Other sizes of nanoparticles can also be used.

The amount of abrasive materials (e.g., diamond particles) included in the dental cements, primers, and sealants can vary. For example, in certain embodiments, the dental cement (or one or more of the base and catalyst components thereof), the dental primer, or the dental sealant comprises between about 0.1% and about 20% by weight of abrasive materials (e.g., diamond particles). In other embodiments, the dental cement (or one or more of the base and catalyst components thereof), dental primer, or dental sealant comprises between about 0.1% and about 15%, between about 0.1% and about 10%, between about 0.1% and about 5%, between about 0.5% and about 2.5%, or between about 1% and about 2.5% by weight of abrasive materials (e.g., diamond particles). Other amounts can also be used.

In some embodiments comprising a dental cement including a base and a catalyst component, both of the base and catalyst components comprise abrasive materials. In other of such embodiments, only one of the base and/or catalyst components comprises abrasive materials (e.g., diamond particles).

The dental cements, primers, and sealants can also comprise a carrier in which the abrasive materials can be dispersed. As discussed above with respect to the dental adhesives, in some embodiments, the carrier comprises a polymerizable material. As further discussed above with respect to the dental adhesives, various types of polymerizable materials, such a monomers, dimers and oligomers, can also be included in the dental cements (or in a base and/or catalyst component thereof), primers, and sealants disclosed herein. Further, it is contemplated that any of the polymerizable materials discussed with regards to dental adhesives can also be used in the dental cements, primers, and sealants. For example, in some embodiments, the dental cement (or one or more of the base and/or catalyst components thereof), dental primer, or dental sealant comprises one or more acrylic monomers, vinyl-containing monomers, silicon-containing monomers, and/or thiol containing monomers. And in certain embodiments, the dental cement (or one or more of the base and/or catalyst components thereof), dental primer, or dental sealant comprises one or more acrylate monomers, acrylamide monomers, or mixtures thereof. In further embodiments, the dental cement (or one or more of the base and/or catalyst components thereof), dental primer, or dental sealant comprises one or more acrylic monomers selected from the group consisting of methacrylate monomers (or methacrylic monomers), methacrylamide monomers, and mixtures thereof. And in still further embodiments, the dental cement (or one or more of the base and/or catalyst components thereof), dental primer, or dental sealant comprises at least one methacrylate monomer (or at least one methacrylic monomer).

The amount of polymerizable materials (e.g., monomers) included in the dental cement (or the base and/or catalyst components thereof), dental primer, or dental sealant can also vary. For example, in one embodiment, the base component can comprise between about 20% and about 95% by weight of one or more polymerizable components, and the catalyst component can comprise between about 20% and about 90% by weight of one or more polymerizable components. Other amounts can also be used.

The cements, primers, and sealants disclosed herein can also include one or more additional components as desired. For instance, the dental cements and dental primers (or one or more of the base and/or catalyst components thereof) can further comprise one or more solvents. The dental cements, primers, and sealants can further comprise one or more initiators and/or accelerators. Any of the solvents, initiators and/or accelerators (e.g., photoinitiators, reducing agents, etc.) identified above with regards to the dental adhesives can be used.

The dental cements (or one or more of the base and/or catalyst components thereof), dental primers, or dental sealants can further include one or more additives. Exemplary additives can include, but are not limited to, preservatives (or polymerization inhibitors), antimicrobial agents, bonding agents, fillers, radiopaque agents, fluorescent agents, and/or ultraviolet absorbing agents. Any of the additives described in relation to the dental adhesives can be used. The dental cements (or one or more of the base and/or catalyst components thereof), dental primers, or dental sealants can also comprise one or more dyes, colorants, or pigments (e.g., titanium dioxide) to modify the optical properties of the dental cement. In other embodiments, the diamond particles (or particles) can exhibit a white color and additional colorants may not be needed.

In certain embodiments, the dental cement comprises a glass ionomer cement. For example, the dental cement can comprise a resin modified glass ionomer cement. In such embodiments, the cement (or a base component thereof) can comprise between about 40% and about 65% by weight of a glass ionomer. Other amounts can also be included.

The dental primers can also include, for example, one or more of each of the polymerizable materials, solvents, initiators, and, optionally, acids. The dental sealants can include, for example, one or more of each of the polymerizable materials, initiators, and fillers. Additional components can also be included, such as solvents, rheology and/or viscosity modifiers, thickening agents, surfactants, etc. Any of the above-identified materials discussed with regards to the dental adhesives can be used.

Methods of using the dental cements, primers, and sealants are also disclosed herein. In particular, it is contemplated that any of the components, principles, and/or embodiments discussed above may be utilized in either a dental cement, primer, or sealant, or a method of using the same. In one embodiment, the method of using a dental cement, primer, or sealant comprises a step of preparing a tooth surface (which can be similar to the step described above with respect to dental adhesives). The method can further comprise a washing or rinsing step, and an optional drying step (which can also be similar to the steps described above with respect to dental adhesives).

In certain embodiments, the method can also comprise an optional step of applying an etchant to an exposed surface of the tooth structure. After an etchant is applied to the tooth structure, an abrasion or scrubbing step can optionally be performed. In one embodiment, after the etchant has been used to etch, abrade away or otherwise remove a portion of the tooth structure, dental smear, and/or other debris, the etchant can be removed (e.g., washed or rinsed).

The method can further comprise an adhering step. For example, the dental cement, primer, or sealant can be disposed on a surface of the tooth structure. The dental cement, primer, or sealant can also penetrate and/or otherwise extend into one or more of the dentin tubules and/or enamel. In embodiments using a dental primer, a dental cement or adhesive can also be disposed over the dental primer. With the dental primer and/or cement in place, a dental structure or dental restorative material can be placed in contact with the dental primer and/or cement as it is applied to the tooth structure. The dental cement, primer, or sealant can then be cured to adhere or otherwise bond the dental structure or restorative material to the tooth structure. In some embodiments, the dental cement can be cured with a dental curing light. For example, in certain embodiments, a curing light is applied to the dental cement for between about 1 and about 30 seconds, such as for at least about 3 seconds, 5 seconds, 8 seconds, 10 seconds, or 15 seconds to at least partially cure the dental cement. In certain embodiments, the dental cement and/or primer is at least partially cured before adhering the dental structure or dental restorative material.

It will be appreciated that the dental cement, primer, or sealant can be applied to a surface of a tooth structure and/or a dental structure or dental restoration material. For example, the dental cement, primer, or sealant can be applied to a surface of a dental restoration material in a manner that is analogous to applying the dental adhesive to the surface of a tooth. The dental cement, primer, or sealant can also be applied to a surface of the dental structure (tooth structure and/or dental restoration material) and used to abrade away or otherwise prepare the surface for bonding (e.g., by rubbing, scrubbing, etc.). It will thus be appreciated that various methods are contemplated, and that the methods of using the dental cement, primer, or sealant are not limited to the above-identified steps.

As set forth above, in another embodiment, the present disclosure relates to dental etchants. The dental etchants disclosed herein can be used as traditional etchants used in the dental industry. For instance, the dental etchants can be used in dental restoration and/or restorative procedures. In particular embodiments, the dental etchants can be used to prepare a tooth structure and/or dental restoration material prior to bonding another dental structure onto the tooth and/or dental restoration material. For instance, a dental etchant can be applied to a surface of a first dental structure upon which the dental etchant is configured to abrade, etch, or abrade and etch at least a portion of the surface. A second dental structure can thereafter be bonded or adhered to the first dental structure.

Various types of dental etchants are contemplated, including mechanical etchants, chemical etchants, and mechanical and physical etchants. The etchants can comprise one or more abrasive materials or abrasive agents. The etchants can further comprise a carrier in which the abrasive materials can be dispersed. In some embodiments, the dental etchants further comprises an acid etching agent. Additional components can also be included, such as solvents, rheology and/or viscosity modifiers, thickening agents, surfactants, etc.

Without limitation, it will be appreciated that the particular components identified above for use with dental adhesives and/or dental cements, primers, and sealants can also be incorporated into the dental etchants. For example, various types of abrasive materials can be included in the dental etchants disclosed herein. In particular, it is contemplated that any of the abrasive materials discussed above with respect to the dental adhesives can also be used in a dental etchant. For example, the abrasive materials can comprise diamond particles, microparticles, and/or nanoparticles.

In some embodiments, the dental etchants comprise diamond nanoparticles having an average size of between about 0.5 nm and about 100 nm, between about 1 nm and about 50 nm, or between about 5 nm and about 10 nm. In further embodiments, the dental etchants comprise diamond nanoparticles having an average size of less than about 50 nm, less than about 20 nm, or less than about 10 nm. Other sizes of nanoparticles can also be used.

The amount of abrasive materials (e.g., diamond particles) included in the dental etchants can vary. For example, in certain embodiments, the dental etchants comprise between about 0.1% and about 20% by weight of abrasive materials (e.g., diamond particles). In other embodiments, the dental etchants comprises between about 0.1% and about 15%, between about 0.1% and about 10%, between about 0.1% and about 5%, between about 0.5% and about 5%, between about 0.5% and about 2.5%, or between about 1% and about 2.5% by weight of abrasive materials (e.g., diamond particles). Other amounts can also be used.

The dental etchants can further comprise one or more additional components as desired. For instance, in some embodiments, the dental etchants comprise a carrier. The carrier can include one or more solvents (e.g., polar solvents such as water, ethanol, and/or acetone). The dental etchants can further include surfactants, rheology and/or viscosity modifiers, thickening agents, preservatives, antimicrobials, colorants, pigments, and/or fillers, etc.

In certain embodiments, the dental etchants can be configured as a mechanical etchant and a chemical etchant. In such embodiments, the mechanical etch properties can be provided by the abrasive materials (e.g., which can be rubbed on the tooth or structural surface). The chemical etch properties can be provided by one or more acids (or acid etching agents). Exemplary acids that can be used in the dental etchants include, but are not limited to, phosphoric acid and/or hydrofluoric acid. Other acids can also be used. In some embodiments, the etchant comprises between about 30% and about 50% by weight of acid etching agents. In other embodiments, the etchant is configured as a mechanical etchant and is devoid of acid etching agents.

The dental etchants can thus be configured to abrade, etch, or abrade and etch at least a portion of a surface of a tooth or dental structure to which it is applied. In some embodiments, the dental etchants are configured to abrade and etch a portion of the surface. In other embodiments, the dental etchants are only configured to abrade (e.g., when scrubbed), or only configured to etch (e.g., via an acid etching agent).

Methods of using the dental etchants are also disclosed herein. In particular, it is contemplated that any of the components, principles, and/or embodiments discussed above may be utilized in either a dental etchant or a method of using the same. In one embodiment, the method of using a dental etchant comprises a step of preparing a tooth surface (similar to the step described above with respect to dental adhesives). The method can also comprise a washing or rinsing step, and an optional drying step (similar to the steps described above with respect to dental adhesives).

The method can also comprise an abrading and/or etching step that includes applying a dental etchant to an exposed surface of a tooth or other dental structure. In some embodiments, the abrading and/or etching step optionally comprises an abrasion or scrubbing step (e.g., for mechanically etching the surface). In one embodiment, after the dental etchant has been used to abrade away or otherwise remove a portion of the tooth (e.g., including dental smear and other debris) or dental structure, the etchant can be removed (rinsed and/or washed). In other embodiments, such as embodiments devoid of acid etching agents, the dental etchant can remain on the tooth or dental structure surface after which an adhesion step can be performed. For instance, a second dental structure can be adhered to the tooth or first dental structure. Additional steps and/or methods can also be employed.

Without limitation, it will be appreciated that the compositions disclosed herein (e.g., adhesives, cements, primers, sealants, etchants) can be non-toxic and safe for human use and/or consumption. Further, the abrasive materials (e.g., diamond particles) can be dispersed throughout the composition. And in certain embodiments, the abrasive materials can be dispersed throughout the in a uniform or substantially uniform manner.

It will also be appreciated that the various compositions can be used individually or in combination with one another. For instance, it will be appreciated that one or more of the adhesives, cements, primers, sealants, and/or etchants disclosed herein could be used in combination with one or more of the other disclosed compositions (e.g., an etchant could be used with a cement, etc.).

EXAMPLES

The following examples are illustrative and not intended to be limiting in any way.

Example 1

A sample dental adhesive composition was prepared by mixing together the components listed in Table I:

TABLE I

| Component: | Amount (wt %) |
|---|---|
| Polymerizable Materials | 70-80 |
| Solvent(s) | 10-20 |
| Initiator(s)/Accelerator(s) | 0.5-2.5 |
| Preservative(s) | 0.05-0.25 |
| Filler | 1-5 |
| Diamond Particles | 5 |

The dental adhesive composition was then rubbed and/or scrubbed over the surface of a tooth structure covered in dental smear using a dental brush tip, such as the Inspiral® brush tip (commercially available from Ultradent Products, Inc.), for two intervals of 10 seconds each. After scrubbing the tooth surface, the tooth structure was washed with water to remove the dental adhesive composition from the tooth surface. An image of the tooth surface was taken using scanning electron microscopy and is shown in FIG. 1 (magnification 1000×).

As shown in FIG. 1, the dental adhesive successfully removed a portion of the smear layer. The dentin tubules are also visible, indicating that the dental adhesive also successfully removed at least a portion of the smear layer from the dentin tubules.

Example 2

A sample dental adhesive composition was prepared by mixing together the components listed in Table II:

TABLE II

| Component: | Amount (wt %) |
| --- | --- |
| Polymerizable Materials | 70-80 |
| Solvent(s) | 10-20 |
| Initiator(s)/Accelerator(s) | 0.5-2.5 |
| Preservative(s) | 0.05-0.25 |
| Filler | 3-8 |
| Diamond Particles | 2.5 |

The dental adhesive composition was then rubbed and/or scrubbed over the surface of a tooth structure covered in dental smear using a dental brush tip, such as the Inspiral® brush tip (commercially available from Ultradent Products, Inc.), for two intervals of 10 seconds each. After scrubbing the tooth surface, the tooth structure was washed with water to remove the dental adhesive composition from the tooth surface. An image of the tooth surface was taken using scanning electron microscopy and is shown in FIG. 2 (magnification 1000×).

Figure 2:
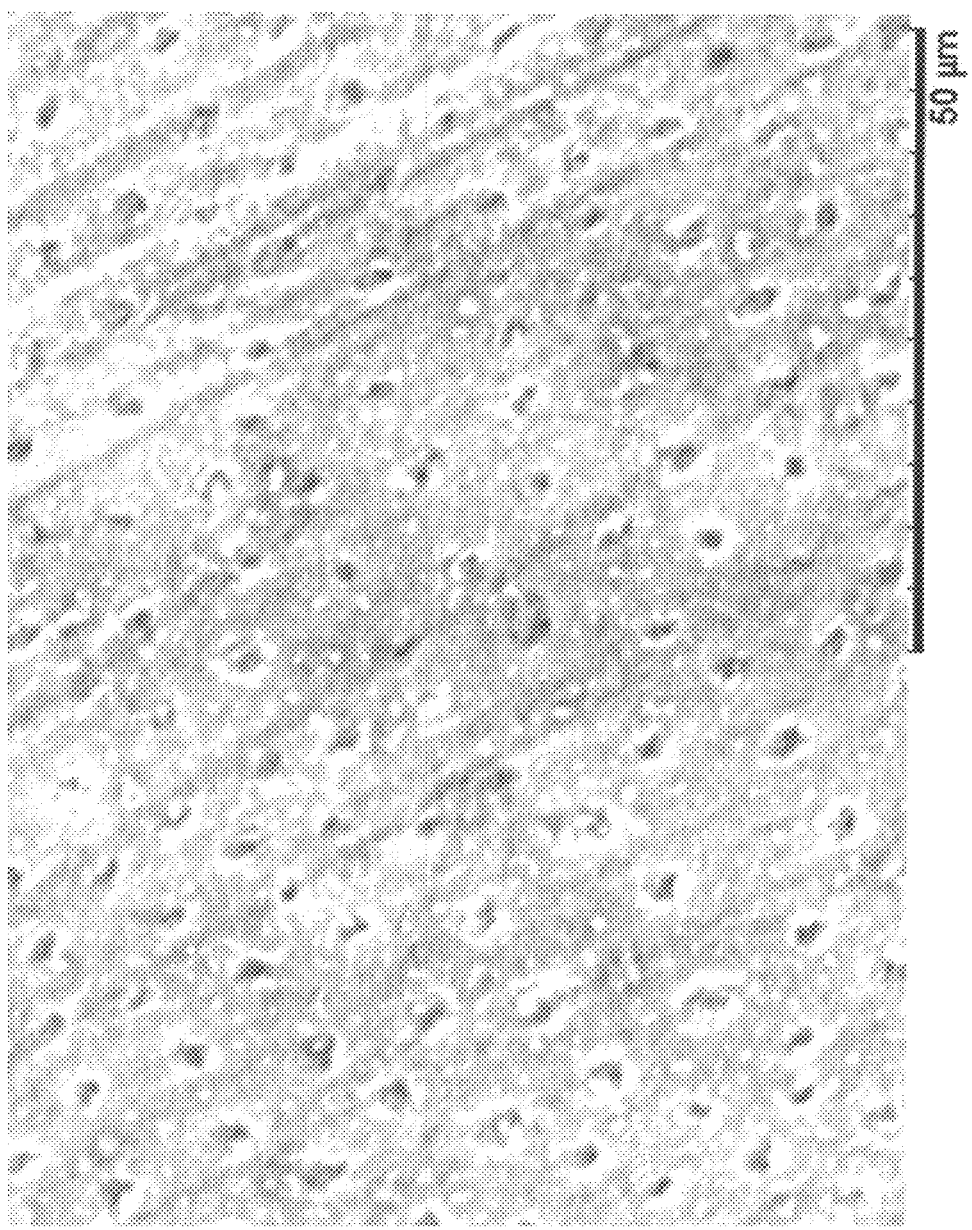
FIG. 2 is an image of a tooth surface after treatment with an adhesive composition in accordance with another embodiment of the present disclosure.

As shown in FIG. 2, the dental adhesive successfully removed a portion of the smear layer. The dentin tubules are also visible, indicating that the dental adhesive also successfully removed at least a portion of the smear layer from the dentin tubules. As compared to FIG. 1, less of the smear layer was removed from the dentin tubules and/or the surface of the tooth structure.

Example 3

A sample dental adhesive composition was prepared by mixing together the components listed in Table III:

TABLE III

| Component: | Amount (wt %) |
| --- | --- |
| Polymerizable Materials | 70-80 |
| Solvent(s) | 10-20 |
| Initiator(s)/Accelerator(s) | 0.5-2.5 |
| Preservative(s) | 0.05-0.25 |
| Filler | 5-10 |
| Diamond Particles | 0.5 |

The dental adhesive composition was then rubbed and/or scrubbed over the surface of a tooth structure covered in dental smear using a dental brush tip, such as the Inspiral® brush tip (commercially available from Ultradent Products, Inc.), for two intervals of 10 seconds each. After scrubbing the tooth surface, the tooth structure was washed with water to remove the dental adhesive composition from the tooth surface. An image of the tooth surface was taken using scanning electron microscopy and is shown in FIG. 3 (magnification 1000×).

Figure 3:
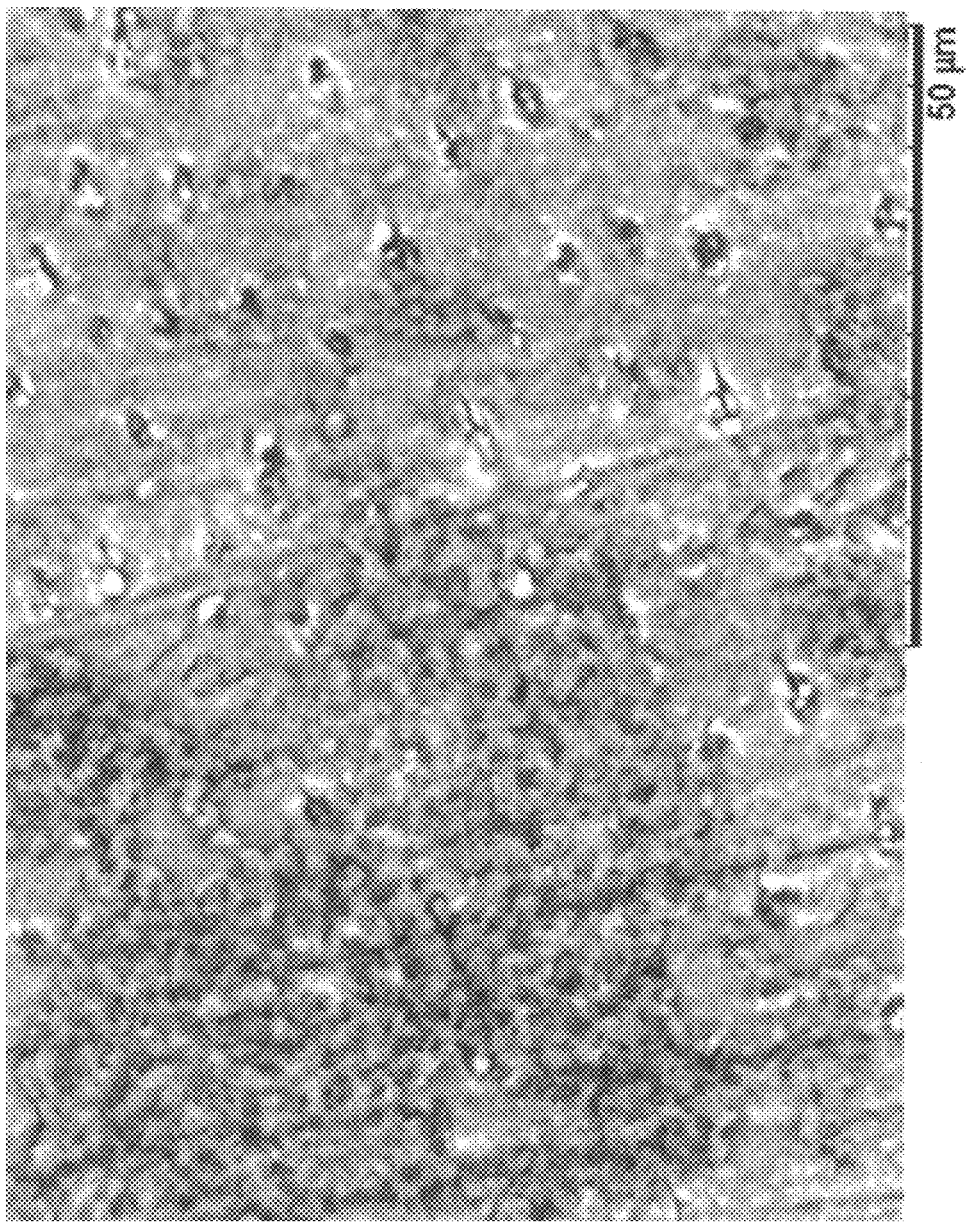
FIG. 3 is an image of a tooth surface after treatment with an adhesive composition in accordance with another embodiment of the present disclosure.

As shown in FIG. 3, the dental adhesive removed a portion of the smear layer. The dentin tubules are also visible, indicating that the dental adhesive also removed at least a portion of the smear layer from the dentin tubules. As compared to FIGS. 1 and 2, less of the smear layer was removed from the dentin tubules and/or the surface of the tooth structure.

Example 4

A comparative sample dental adhesive composition devoid of diamond particles was prepared by mixing together the components listed in Table IV:

TABLE IV

| Component: | Amount (wt %) |
| --- | --- |
| Polymerizable Materials | 70-80 |
| Solvent(s) | 10-20 |
| Initiator(s)/Accelerator(s) | 0.5-2.5 |
| Preservative(s) | 0.05-0.25 |
| Filler | 5-10 |
| Diamond Particles | 0 |

The dental adhesive composition was then rubbed and/or scrubbed over the surface of a tooth structure covered in dental smear using a dental brush tip, such as the Inspiral® brush tip (commercially available from Ultradent Products, Inc.), for two intervals of 10 seconds each. After scrubbing the tooth surface, the tooth structure was washed with water to remove the dental adhesive composition from the tooth surface. An image of the tooth surface was taken using scanning electron microscopy and is shown in FIG. 4 (magnification 1000×).

Figure 4:
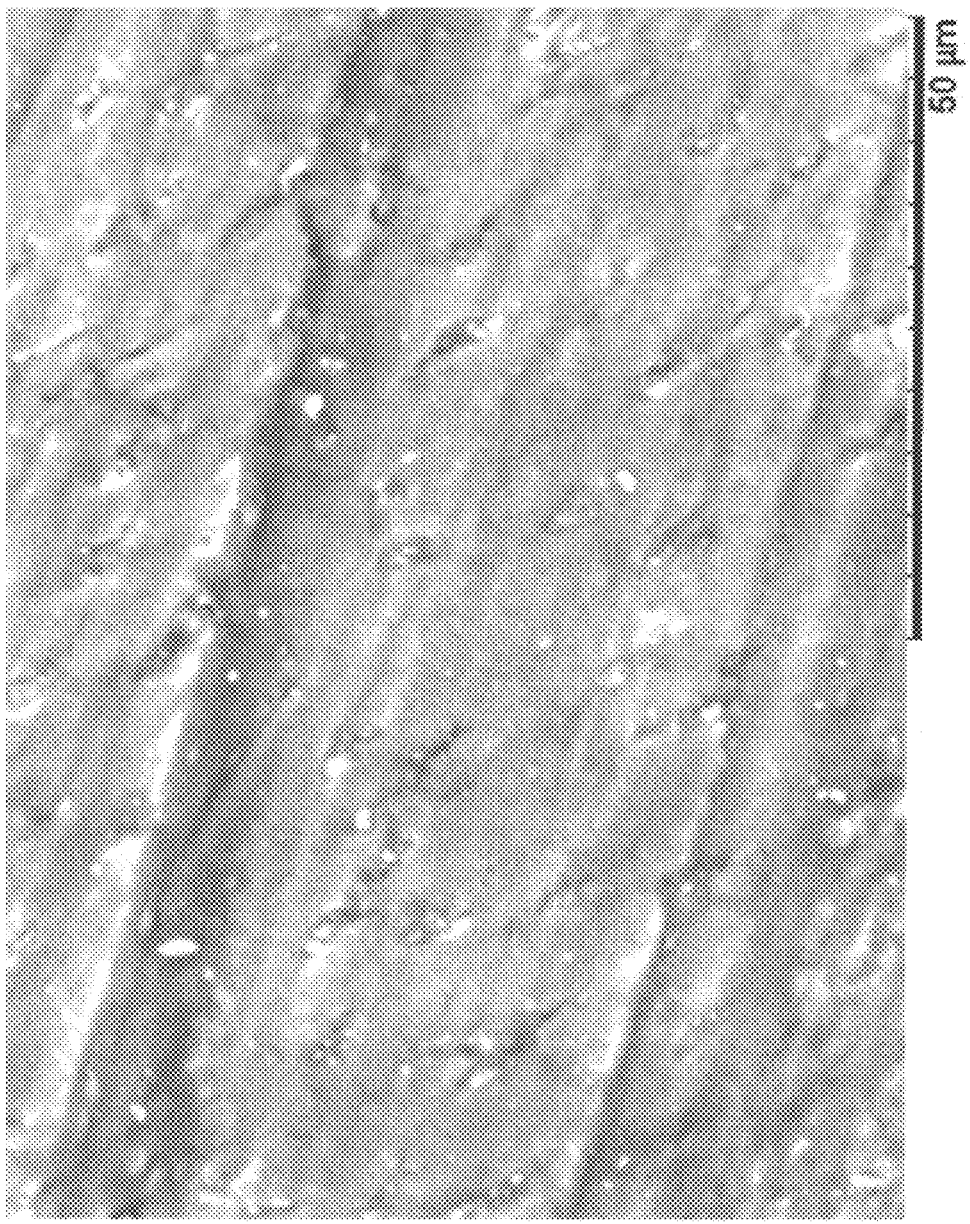
FIG. 4 is an image of a tooth surface after treatment with a comparative adhesive composition.

As shown in FIG. 4, little to no smear material was removed by the dental adhesive. The dentin tubules are barely visible, indicating that the dental adhesive removed little to no smear material from the dentin tubules. As compared to FIGS. 1, 2 and 3, significantly less of the smear layer was removed from the dentin tubules and/or the surface of the tooth structure.

Example 5

A resin dental cement composition can be prepared with the base and catalyst components listed in Tables V and VI:

TABLE V

| (Base Component): | |
| --- | --- |
| Component: | Amount (wt %) |
| Polymerizable Materials | 45-95 |
| Preservative(s) | 0.1-1 |
| Initiator(s)/Accelerator(s) | 0.1-2 |
| Rheology and/or Viscosity Modifier(s) | 0.1-10 |
| Filler | 30-90 |
| Diamond Particles | 0.1-10 |

TABLE VI

| (Catalyst Component): | |
| --- | --- |
| Component: | Amount (wt %) |
| Polymerizable Materials | 15-60 |
| Initiator(s)/Accelerator(s) | 0.1-4 |
| Rheology and/or Viscosity Modifier(s) | 0.1-10 |
| Filler | 30-90 |
| Diamond Particles | 0.1-10 |

Prior to use, the base and catalyst components can be mixed and thereafter applied to a tooth or dental structure.

Example 6

A glass ionomer dental cement composition can be prepared with the base and catalyst components listed in Tables VII and VIII:

TABLE VII (Base Component):

| Component: | Amount (wt %) |
|---|---|
| Polymerizable Materials | 10-60 |
| Solvent(s) | 0.1-5 |
| Preservative(s) | 0.1-1 |
| Initiator(s)/Accelerator(s) | 0.1-5 |
| Radiopaque Agent | 5-15 |
| Glass Ionomer(s) | 40-65 |
| Filler | 0.1-10 |
| Diamond Particles | 0.1-10 |

TABLE VIII (Catalyst Component):

| Component: | Amount (wt %) |
|---|---|
| Polymerizable Materials | 45-90 |
| Initiator(s)/Accelerator(s) | 0.1-4 |
| Rheology and/or Viscosity Modifier(s) | 10-50 |
| Radiopaque Agent | 0.1-10 |
| Filler | 0.1-10 |
| Diamond Particles | 0.1-10 |

Prior to use, the base and catalyst components can be mixed and thereafter applied to a tooth or dental structure.

Example 7

A dental etchant composition can be prepared with components listed in Table IX:

TABLE IX

| Component: | Amount (wt %) |
|---|---|
| Solvent | 30-60 |
| Acid Etching Agent | 30-50 |
| Diamond Particles | 0.1-10 |
| Rheology and/or Viscosity Modifier(s) | 5-40 |
| Surfactant | 0.1-5 |

The dental etchant can be used to mechanically and chemically abrade and etch a tooth or other dental structure as desired.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A dental method, comprising:
applying a dental composition to a surface of a dental structure, wherein the dental composition comprises one or more polymerizable materials and one or more abrasive materials, wherein the abrasive materials comprise one or more of diamond particles, fullerene particles, graphene particles, lonsdaleite particles, or cubic boron nitride particles;
scrubbing the dental composition over the surface of the dental structure to abrade a portion of the surface; and
adhering a second dental structure onto the surface with the dental composition.

2. The method of claim 1, wherein the abrasive materials comprise at (Original) least one of diamond particles, diamond microparticles, or diamond nanoparticles.

3. The method of claim 2, wherein the abrasive materials comprise diamond nanoparticles having an average size of between about 0.5 nm and about 100 nm.

4. The method of claim 1, wherein the dental composition comprises a dental cement comprising a base component and a catalyst component.

5. The method of claim 4, wherein the base component comprises a glass ionomer.

6. The method of claim 5, wherein the base component comprises from about 40% to about 65% by weight of the glass ionomer.

7. The method of claim 1, wherein the dental composition comprises a one-part dental adhesive.

8. The method of claim 1, wherein the dental composition comprises from about 0.1% to about 20% by weight of abrasive materials.

9. The method of claim 1, wherein the dental composition comprises from about 20% to about 95% by weight of the one or more polymerizable materials.

10. The method of claim 1, wherein the one or more polymerizable materials comprise acrylate monomers, acrylamide monomers, or mixtures thereof.

11. A dental method, comprising:
applying a dental composition to a surface of a dental structure, wherein the dental composition comprises one or more polymerizable materials and one or more abrasive materials, wherein the abrasive materials comprise at least one of diamond particles, diamond microparticles, or diamond nanoparticles;
scrubbing the dental composition over the surface of the dental structure to abrade a portion of the surface; and
adhering a second dental structure onto the surface with the dental composition.

12. The method of claim 11, wherein the dental composition comprises a dental cement comprising a base component and a catalyst component.

13. The method of claim 12, wherein the base component comprises a glass ionomer.

14. The method of claim 13, wherein the base component comprises from about 40% to about 65% by weight of the glass ionomer.

15. The method of claim 11, wherein the dental composition comprises a one-part dental adhesive.

16. The method of claim 11, wherein the abrasive materials comprise diamond nanoparticles having an average size of between about 0.5 nm and about 100 nm.

17. The method of claim 11, wherein the dental composition comprises from about 0.1% to about 20% by weight of abrasive materials.

18. The method of claim 11, wherein the dental composition comprises from about 20% to about 95% by weight of the one or more polymerizable materials.

19. The method of claim 11, wherein the one or more polymerizable materials comprise acrylate monomers, acrylamide monomers, or mixtures thereof.

20. A dental method, comprising:
applying a dental composition to a surface of a dental structure, wherein the dental composition comprises one or more polymerizable materials and one or more abrasive materials, wherein the abrasive materials comprise diamond nanoparticles having an average size of between about 0.5 nm and about 100 nm, and wherein the dental composition comprises from about 0.1% to about 20% by weight of abrasive materials;
scrubbing the dental composition over the surface of the dental structure to abrade a portion of the surface; and
adhering a second dental structure onto the surface with the dental composition.

* * * * *